US011246566B2

(12) United States Patent
Andersen et al.

(10) Patent No.: US 11,246,566 B2
(45) Date of Patent: Feb. 15, 2022

(54) US IMAGING PROBE WITH AN INSTRUMENT CHANNEL

(71) Applicant: B-K Medical Aps, Herlev (DK)

(72) Inventors: Marianne Andersen, Bryderupvej (DK); Henrik Jensen, Bagsvaerd (DK); Johannes Paede, Hamburg (DE)

(73) Assignee: B-K MEDICAL APS, Herlev (DK)

( * ) Notice: Subject to any disclaimer, the term of this patent is extended or adjusted under 35 U.S.C. 154(b) by 783 days.

(21) Appl. No.: 15/739,295

(22) PCT Filed: Jun. 26, 2015

(86) PCT No.: PCT/IB2015/054836
§ 371 (c)(1),
(2) Date: Dec. 22, 2017

(87) PCT Pub. No.: WO2016/207701
PCT Pub. Date: Dec. 29, 2016

(65) Prior Publication Data
US 2018/0185007 A1    Jul. 5, 2018

(51) Int. Cl.
*A61B 8/00* (2006.01)
*A61B 8/12* (2006.01)
*A61B 1/00* (2006.01)
*A61B 1/31* (2006.01)
*A61B 1/12* (2006.01)

(52) U.S. Cl.
CPC .......... *A61B 8/445* (2013.01); *A61B 1/00073* (2013.01); *A61B 1/31* (2013.01); *A61B 8/12* (2013.01); *A61B 8/4281* (2013.01); *A61B 8/4494* (2013.01); *A61B 1/126* (2013.01)

(58) Field of Classification Search
CPC .......... A61B 1/12–125; A61B 1/00002; A61B 1/00131–0014; A61B 1/00142–00144; A61B 1/126; A61B 8/445; A61B 1/31; A61B 8/4494; A61B 8/4281; A61B 8/12; A61B 1/00073; A61B 8/00
See application file for complete search history.

(56) References Cited

U.S. PATENT DOCUMENTS 3,760,810 A * 9/1973 Van Hoorn ...... A61B 17/12013
606/140
4,327,738 A * 5/1982 Green .................... A61B 1/042
348/65

(Continued)

OTHER PUBLICATIONS

International Search Report for PCT/IB2015/054836 published as WO2016/207701A1 dated Dec. 29, 2016.

*Primary Examiner* — Oommen Jacob
(74) *Attorney, Agent, or Firm* — Daugherty & Del Zoppo, Co. LPA

(57) ABSTRACT

A system (1100) includes an ultrasound imaging probe (304) with an elongate shaft (312) including an outer perimeter housing (331), two ends (328, 330) and a long axis (320). The system further includes a channel (326) that extends along the direction of the long axis, is part of the outer perimeter housing, and is configured as a recess of the outer perimeter housing. The system further includes a handle (310) affixed to one of the ends of the elongate shaft. The system further includes a transducer array (322) disposed at another of the ends of the elongate shaft. The transducer array includes one or more transducer elements (324).

23 Claims, 7 Drawing Sheets

(56) References Cited

U.S. PATENT DOCUMENTS

| | | | | |
|---|---|---|---|---|
| 4,646,722 | A | * | 3/1987 | Silverstein ......... A61B 1/00073 600/104 |
| 4,815,470 | A | * | 3/1989 | Curtis ................ A61B 1/00142 600/459 |
| 4,823,812 | A | * | 4/1989 | Eshel ...................... A61F 7/12 607/156 |
| 4,877,033 | A | * | 10/1989 | Seitz, Jr. ............ A61B 1/00142 600/441 |
| 4,944,287 | A | * | 7/1990 | Takahashi ............. B21C 37/154 420/401 |
| 4,974,590 | A | * | 12/1990 | Saito ........................ A61B 8/12 600/462 |
| RE34,110 | E | * | 10/1992 | Opie .................. A61B 1/00071 600/123 |
| 5,193,525 | A | * | 3/1993 | Silverstein ......... A61B 1/00096 600/123 |
| 5,207,213 | A | * | 5/1993 | Auhll ................ A61B 1/00091 600/104 |
| 5,349,941 | A | * | 9/1994 | Hori .................. A61B 1/00105 600/122 |
| 5,471,988 | A | * | 12/1995 | Fujio ........................ A61B 8/12 600/439 |
| 5,830,127 | A | * | 11/1998 | DeCastro ............... A61B 1/122 600/157 |
| 5,944,654 | A | * | 8/1999 | Crawford ............... A61B 1/127 600/157 |
| 6,036,649 | A | * | 3/2000 | Yuasa ................. A61B 8/0833 600/462 |
| 6,053,934 | A | * | 4/2000 | Andrews ............ A61B 17/2909 606/207 |
| 6,126,607 | A | * | 10/2000 | Whitmore, III ......... A61B 8/12 600/459 |
| 6,261,234 | B1 | * | 7/2001 | Lin ..................... A61B 8/0833 600/461 |
| 6,340,344 | B1 | * | 1/2002 | Christopher ....... A61B 1/00073 600/127 |
| 6,443,902 | B1 | * | 9/2002 | Sasady ................. A61B 8/0833 600/461 |
| 6,511,427 | B1 | * | 1/2003 | Sliwa, Jr. ............. A61B 5/4869 600/438 |
| 6,533,720 | B1 | * | 3/2003 | Dhindsa ............. A61B 1/00068 600/105 |
| 6,585,642 | B2 | * | 7/2003 | Christopher ....... A61B 1/00073 600/153 |
| 6,626,855 | B1 | * | 9/2003 | Weng ....................... A61B 8/12 600/439 |
| 7,615,005 | B2 | * | 11/2009 | Stefanchik ......... A61B 1/00073 600/104 |
| 7,762,949 | B2 | * | 7/2010 | Nakao ................ A61B 1/00105 600/153 |
| 7,811,265 | B2 | * | 10/2010 | Hering .................... A61B 8/12 604/264 |
| 7,815,565 | B2 | * | 10/2010 | Stefanchik ......... A61B 1/00135 600/121 |
| 7,905,830 | B2 | * | 3/2011 | Stefanchik ......... A61B 1/00135 600/121 |
| 8,007,432 | B2 | * | 8/2011 | Vakharia .......... A61B 17/00234 600/104 |
| 8,052,604 | B2 | * | 11/2011 | Lau .......................... A61B 8/12 600/439 |
| 8,100,882 | B2 | * | 1/2012 | Long .................... A61M 25/09 604/528 |
| 9,861,336 | B2 | * | 1/2018 | Munrow ............ A61B 18/1477 |
| 9,999,430 | B2 | * | 6/2018 | Hirsch ............... A61B 17/1633 |
| 2003/0036681 | A1 | * | 2/2003 | Aviv ..................... A61B 1/2733 600/129 |
| 2003/0171678 | A1 | * | 9/2003 | Batten .................. A61B 8/0833 600/443 |
| 2004/0084070 | A1 | * | 5/2004 | Sasaki .................... A61B 90/70 134/166 R |
| 2004/0234924 | A1 | * | 11/2004 | Hickok .................... A61C 3/03 433/119 |
| 2005/0027165 | A1 | * | 2/2005 | Rovegno ................ A61B 1/012 600/154 |
| 2005/0085803 | A1 | * | 4/2005 | Okabe ............ A61B 17/320068 606/28 |
| 2006/0258908 | A1 | * | 11/2006 | Stefanchik ......... A61B 1/00135 600/121 |
| 2007/0066990 | A1 | * | 3/2007 | Marsella ............... A61M 29/02 606/193 |
| 2008/0064962 | A1 | | 3/2008 | Oonuki |
| 2008/0249416 | A1 | * | 10/2008 | Sato .................... A61B 17/3478 600/454 |
| 2009/0036773 | A1 | * | 2/2009 | Lau .................... A61B 17/2202 600/439 |
| 2009/0118729 | A1 | * | 5/2009 | Auth .................. A61B 18/1492 606/42 |
| 2010/0179416 | A1 | * | 7/2010 | Hoey ..................... A61B 18/04 600/411 |
| 2011/0160514 | A1 | * | 6/2011 | Long ...................... A61B 18/16 600/2 |
| 2012/0116222 | A1 | * | 5/2012 | Sawada .......... A61B 17/320068 600/439 |
| 2012/0209114 | A1 | * | 8/2012 | Staalsen ............... A61B 8/4281 600/438 |
| 2013/0006236 | A1 | * | 1/2013 | Greep ................ A61B 18/1477 606/34 |
| 2015/0057646 | A1 | * | 2/2015 | Aljuri .................... A61B 18/04 606/10 |
| 2018/0116495 | A1 | * | 5/2018 | Karpiel, Jr. ............. B05B 13/04 |
| 2018/0185007 | A1 | * | 7/2018 | Andersen ............... A61B 8/445 |

\* cited by examiner

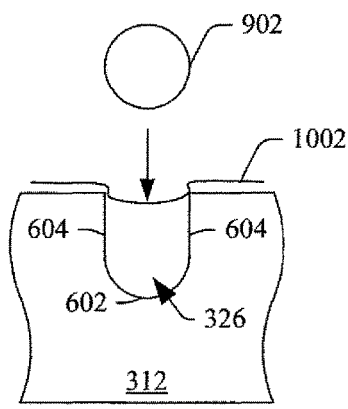
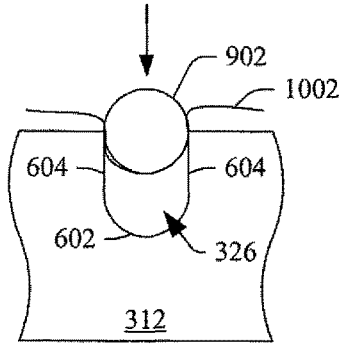
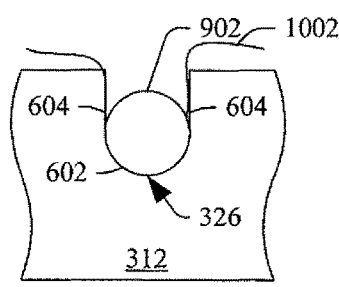
FIGURE 12A  FIGURE 12B  FIGURE 12C
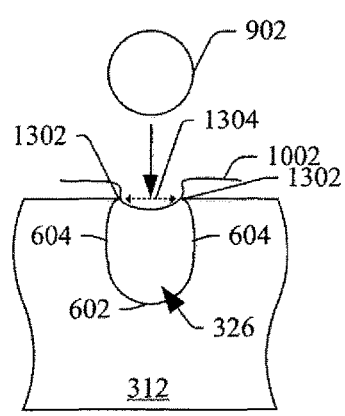
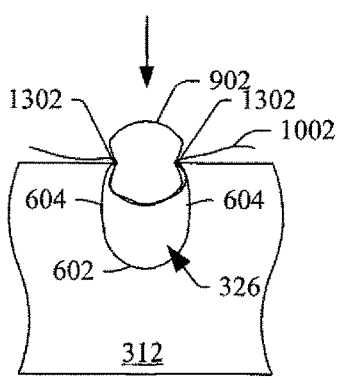
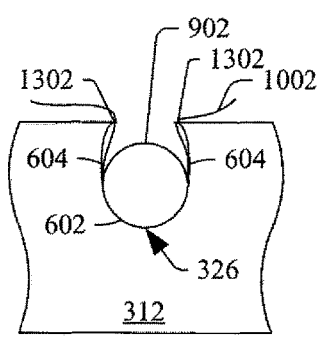
FIGURE 13A  FIGURE 13B  FIGURE 13C
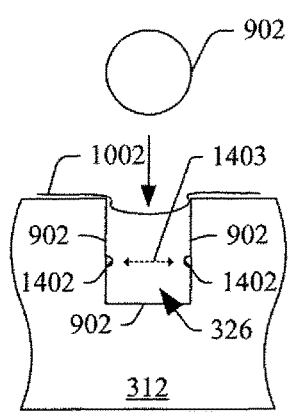
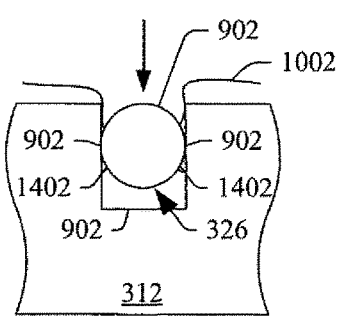
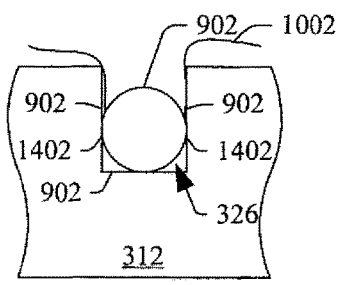
FIGURE 14A  FIGURE 14B  FIGURE 14C

US IMAGING PROBE WITH AN INSTRUMENT CHANNEL

RELATED APPLICATION

This application is a national filing of PCT application Serial No. PCT/IB2015/054836, filed Jun. 26, 2015, published as WO2016/207701 on Dec. 29, 2016. This application claims priority to PCT application Serial No. PCT/IB2015/054836, published as WO2016/207701 on Dec. 29, 2016.

TECHNICAL FIELD

The following generally relates to an ultrasound imaging probe and more particularly to an ultrasound imaging probe with a channel, which is located in at least a shaft of a housing, that is configured to support an external instrument such as tubing for routing an acoustic fluid from outside a cavity to inside of the cavity where the shaft has been inserted.

BACKGROUND

Ultrasound (US) imaging has provided useful information about the interior characteristics (e.g., organ tissue, blood flow, other flow, etc.) of a subject or object under examination. An US imaging system has included an ultrasound probe and a console. The ultrasound probe houses a transducer array, and the console includes a user interface, processing and control circuitry, and either a display or an interface to a display. The transducer array transmits an ultrasound signal into a field of view and receives echoes produced in response to the signal interacting with structure therein. The echoes are processed, producing an image of the scanned structure, which is visually presented through the display monitor. A gel has been applied between the transducer array and the contact area of the subject to improve image quality, as air generally is not a good conductor of ultrasound signals. A suitable gel has acoustic properties well-suited to conduct ultrasound signals between the transducer array and the contact area. For procedures within cavities (e.g., a colorectal procedure), water has been used as the acoustic medium between the transducer array and the contact area.

FIGS. 1 and 2 show an example probe 102 configured for using water as an acoustic medium. The probe 102 includes an elongate shaft 104 extending from a handle region 106. A port 108 located at the handle region 106 interfaces with a hollow path 110 that runs inside of the probe 102 through elongate shaft 104 to an opening 112 at a tip region 114 of the shaft 104. In FIG. 2, a connector 202 at the end of a tube 204 is connected to the port 108. The other end of the tube 204 is connected, through a valve 206, to a syringe 208. In use, an expandable sheath 210 (balloon/water standoff) is placed over the elongate shaft 104 and, in this example, part of the handle 103. An elastic band 212 secures the sheath 210 to the probe 102. The elongate shaft 104 is then inserted into the cavity. The valve 206 is opened, and the syringe 208 is used to pump water into the sheath 210 via water from the syringe 208 and egressing through the opening 112. Once the sheath 210 is suitably filled, e.g., such that it is in contact with the contact area of the subject, the valve 206 is closed. The examination is performed with water as the acoustic medium.

Before using the probe 102 for such an examination, the probe 102 is cleaned, disinfected, sterilized or the like. Any debris (e.g., fecal matter from a colorectal examination) on the probe, e.g., in the hollow path 110, can contaminate the hollow path 110 and/or the tip region 114. After use of the probe 102 for the examination, the water is removed from the cavity by disconnecting the syringe 208 and opening the valve 206, letting the water egress from the cavity out of the tube 204. In this example, the hollow path 110 is entirely inside of the probe 102, with exception of the end at the port 108 and the opening 112. As such, the majority of the hollow path 110 is not readily accessible and/or may be difficult to clean, disinfect, sterilize, etc. for subsequent use for another examination. Furthermore, a protective cover cannot be placed over the hallow path 110 because it would prevent ingress of the water into the sheath 210. Again, any debris (e.g., fecal matter from a colorectal examination) remaining in the hollow path 110 after cleaning, disinfecting, sterilizing, etc. can contaminate the hollow path 110 and/or the tip region 114. Unfortunately, contamination of the hollow path 110 and/or the tip region 114 can transfer to the cavity of a subsequent patient, which may lead to infection. At least in view of the foregoing, there is an unresolved need for another approach.

SUMMARY

Aspects of the application address the above matters, and others.

In one aspect, a system includes an ultrasound imaging probe with an elongate shaft including an outer perimeter housing, two ends and a long axis. The system further includes a channel that extends along the direction of the long axis, is part of the outer perimeter housing, and is configured as a recess of the outer perimeter housing. The system further includes a handle affixed to one of the ends of the elongate shaft. The system further includes a transducer array disposed at another of the ends of the elongate shaft. The transducer array includes one or more transducer elements.

In another aspect, a method includes receiving an acoustic fluid at one end of tubing installed in a recessed channel of an outer surface of an end of an elongate ultrasound imaging probe inserted into a cavity of a subject. The method further includes routing the acoustic fluid through the shaft via the tubing. The method further includes expelling the fluid routed through the shaft into the cavity.

In another aspect, an ultrasound imaging probe includes a tubular section with a long axis and a recess extending along the long axis. The recess has a depth and a width. The ultrasound imaging probe further includes a first end portion affixed to a first end of the tubular section. The ultrasound imaging probe further includes a second end portion affixed to a second opposing end of the tubular section. The ultrasound imaging probe further includes one or more transducer elements disposed at one of the first or second end portions.

Those skilled in the art will recognize still other aspects of the present application upon reading and understanding the attached description.

BRIEF DESCRIPTION OF THE DRAWINGS

The application is illustrated by way of example and not limitation in the figures of the accompanying drawings, in which like references indicate similar elements and in which:

FIGS. 12A, 12B and 12C schematically illustrate example geometry of the recess and installation of tubing therein;

FIGS. 13A, 13B and 13C schematically illustrate another example of geometry of the recess and installation of tubing therein;

FIGS. 14A, 14B and 14C schematically illustrate yet another example of geometry of the recess and installation of tubing therein.

DETAILED DESCRIPTION

Figure 3:
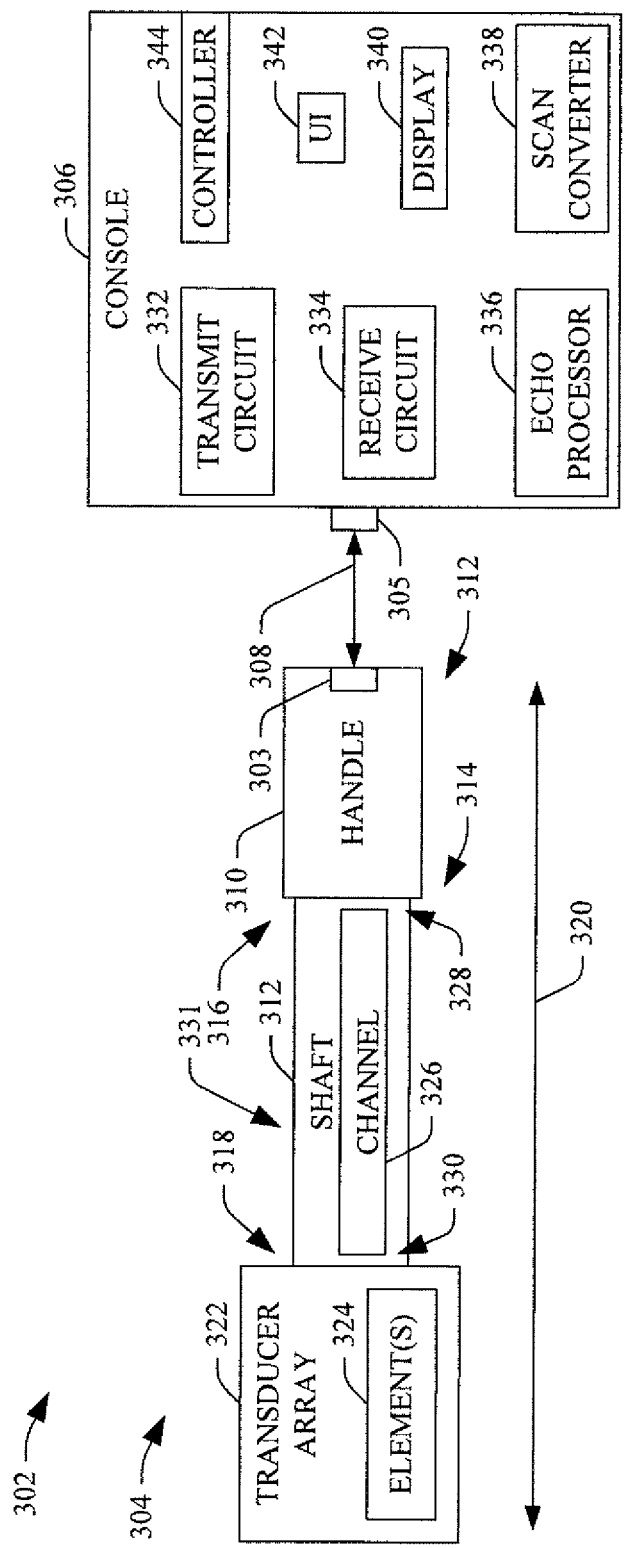
FIG. 3 schematically illustrates an example ultrasound imaging system with a recess in the housing for holding tubing for routing an acoustic medium from outside of a cavity of a patient to inside of the cavity between the transducer array and the contact area of the cavity.

FIG. 3 schematically illustrates an imaging system 302 such as ultrasound imaging system. The imaging system 302 includes an ultrasound imaging probe 304 and a console 306. The ultrasound imaging probe 304 and the console 306 include complementary communication interfaces 303 and 305, which are configured for wireless and/or wired communication between the ultrasound imaging probe 304 and the console 306 over a communication path 308.

The probe 304, in one instance, is configured as a natural orifice probe, which includes probes configured for insertion into a cavity of the body by way of a natural orifice of the body (e.g., anus, vagina, esophagus, eye, ear, nasal cavity, etc.). Additionally or alternatively, the probe 304 is configured for insertion through a non-natural orifice of the body (e.g., an incision, etc.). An example probe is the Type 2052 and the Type 8838, both products of BK-Medical ApS, Herlev, DK, which is a wholly owned subsidiary of Analogic Corporation, MA, USA.

In the illustrated embodiment, the ultrasound imaging probe 304 includes a handle region 310 and an elongate shaft 312. A first side 314 of the handle region 310 includes the communication interface 303. A second side 314 of the handle region 310 is affixed to the elongate shaft 312. The elongate shaft 312 includes a first end region 316 affixed to the handle region 310 and a second end or tip region 318, located opposite the first end region 314 along a long axis 320 of the probe 304 and the elongate shaft 312.

A transducer array 322, with a one-dimensional (1-D) or two-dimensional (2-D) array of transducer elements 324, is disposed at the second end or tip region 318 and can be considered as part of a tip of the shaft 312. The transducer array 322 includes one or more transducer elements 324. The transducer elements 324 are configured to transmit ultrasound signals and receive echo signals. Suitable configurations include, but are not limited to, single element, linear array, curved array, phased array, etc. The transducer array 322 can be fully populated or sparse, square, circular, irregular, etc.

Figure 1:
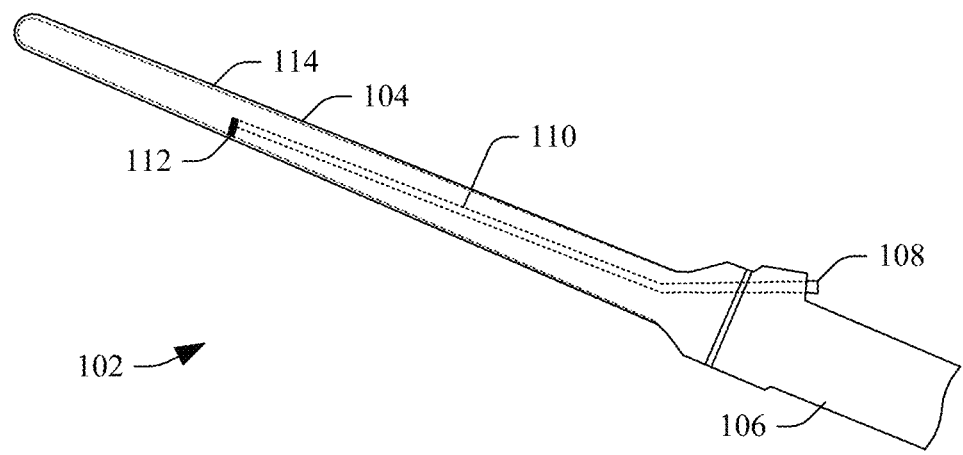
FIGS. 1 and 2 illustrate a prior art ultrasound probe with an internal hollow path for routing an acoustic medium from outside of a cavity of a patient to inside of the cavity between the transducer array and the contact area of the cavity.
Figure 2:
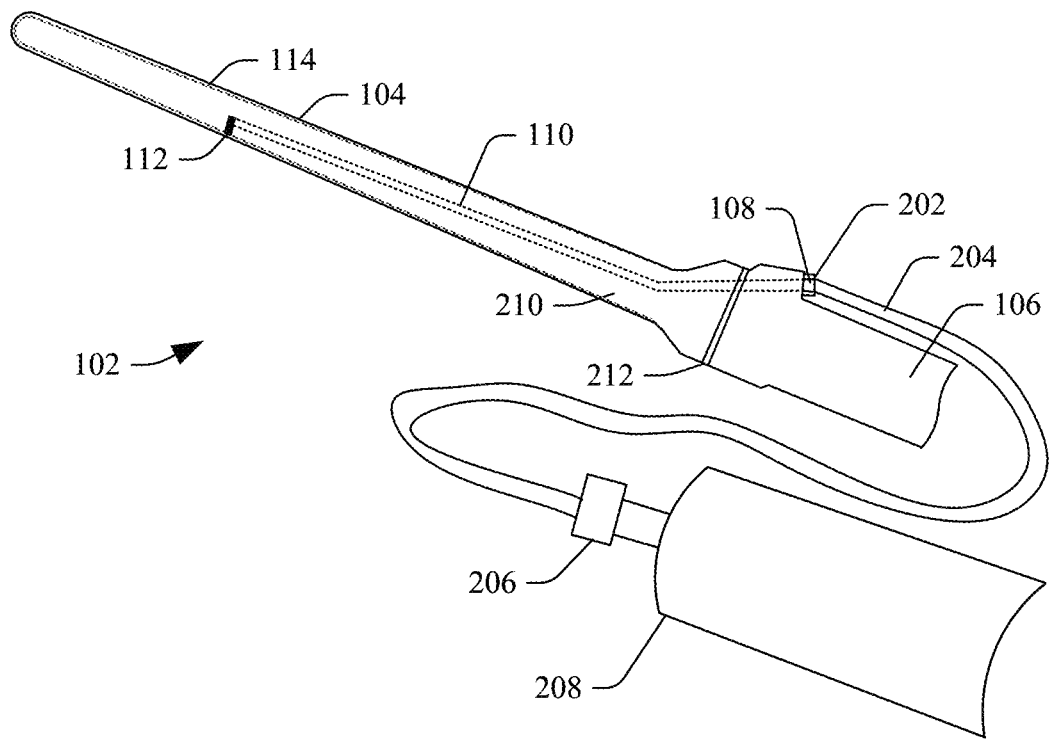

The probe 304 further includes a channel 326 with first and second end regions 328 and 330. As described in greater detail below, the channel 326 is part of an outer perimeter housing 331 of the probe 304 and is configured as a recess in at least the outer perimeter housing 331. In a variation, the channel 326 extends to also be part of at least the handle end 310 of the probe 304. Unlike the hollow pathway 110 of FIGS. 1 and 2, which is fully inside of the probe 102 (with the exception of the portion at the port 108 and at the opening 112), the channel 326 is an open recess (e.g., open to the ambient environment) and not enclosed inside of the shaft 312 or other parts of the probe 304. Such a configuration renders the channel 326 easier to clean, disinfect, and/or sterilize, relative to a configuration in which the channel is enclosed inside the probe 304. It is also possible to use a cover as the tube is on the outside.

Also described in greater detail below, generally, the channel 326 is geometrically configured to receive an instrument such as tubing configured to route a fluid, such as water, from outside of a cavity of a subject or object, into which the shaft 312 is inserted, to inside of the cavity. Such fluid can be used to fill and expand an elastic expandable container such as a balloon, standoff, etc. installed over the shaft 312 in the cavity or is applied directly in the cavity, e.g., in connection with a live water injection procedure. The fluid provides an acoustic medium for ultrasound signals between the transducer elements 324 of the transducer array 322 and the tissue inside of the cavity. Other instruments are also contemplated herein.

The console 306 includes transmit circuitry 332 configured to generate a set of radio frequency (RF) pulses that are conveyed to the transducer array 322. The set of pulses actuates a corresponding set of the transducer elements 324, causing one or more sets of the elements 324 to transmit ultrasound signals into an examination or scan field of view.

The console 306 further includes receive circuitry 334 configured to receive echoes (RF signals) generated in response to the transmitted ultrasound signals from the transducer array 322. The echoes, generally, are a result of the interaction between the emitted ultrasound signals and the structure (e.g., flowing blood cells, organ cells, etc.) in the scan field of view.

The console 306 further includes an echo processor 336 that processes received echoes. Such processing may include applying time delays, weighting on the channels, summing, and/or otherwise beamforming received echoes. Other processing may lower speckle, improve specular reflector delineation, and/or includes FIR filtering, IIR filtering, etc. For B-mode, the echo processor 336 generates a sequence of focused, coherent echo samples along focused scanlines of a scanplane.

The console 306 further includes a scan converter 338 that scan converts the frames of data to generate data for display, for example, by converting the data to the coordinate system of a display 340, which may be integrated with the console (as shown) or a separate device therefrom. The scan converter 338 can use analog and/or digital scan converting techniques.

The console 306 further includes a user interface (UI) 342 with one or more input devices (e.g., a button, a knob, a touchscreen, etc.) and/or one or more output devices (e.g., the display 340, communication ports, etc.), which allows for interaction with the system 302.

The console 306 further includes a controller 344 that controls at least one of transducer array 322, the element(s) 324, the transmit circuit 332, the receive circuit 334, the echo processor 336, the scan converter 338, the display 340 or the user interface 342.

At least one of the components of the console 306 can be implemented by a processor (e.g., a microprocessor, a central processing unit, etc.) executing computer readable instructions encoded, embedded, stored, etc. on non-transitory computer readable storage medium such as physical memory. In a variation, the at least one of the components is implemented by the processor executing computer readable instructions carried by a signal, carrier medium and/or other transitory computer readable storage medium.

Figure 4:
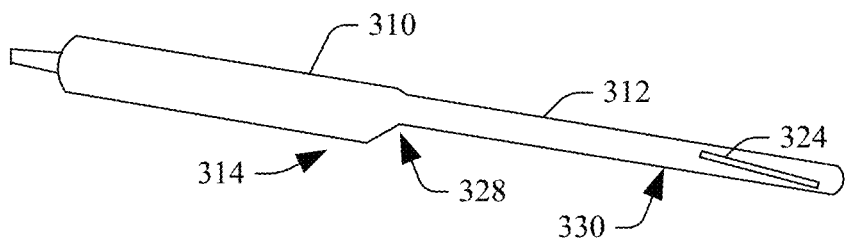
FIG. 4 illustrate a perspective view of an example of the probe of FIG. 3.
Figure 5:
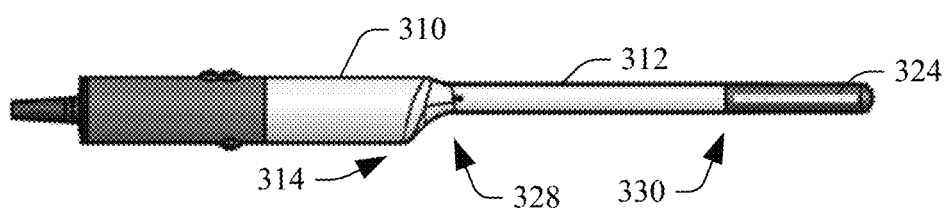
FIG. 5 illustrate a side view of the probe of FIG. 4.
Figure 6:
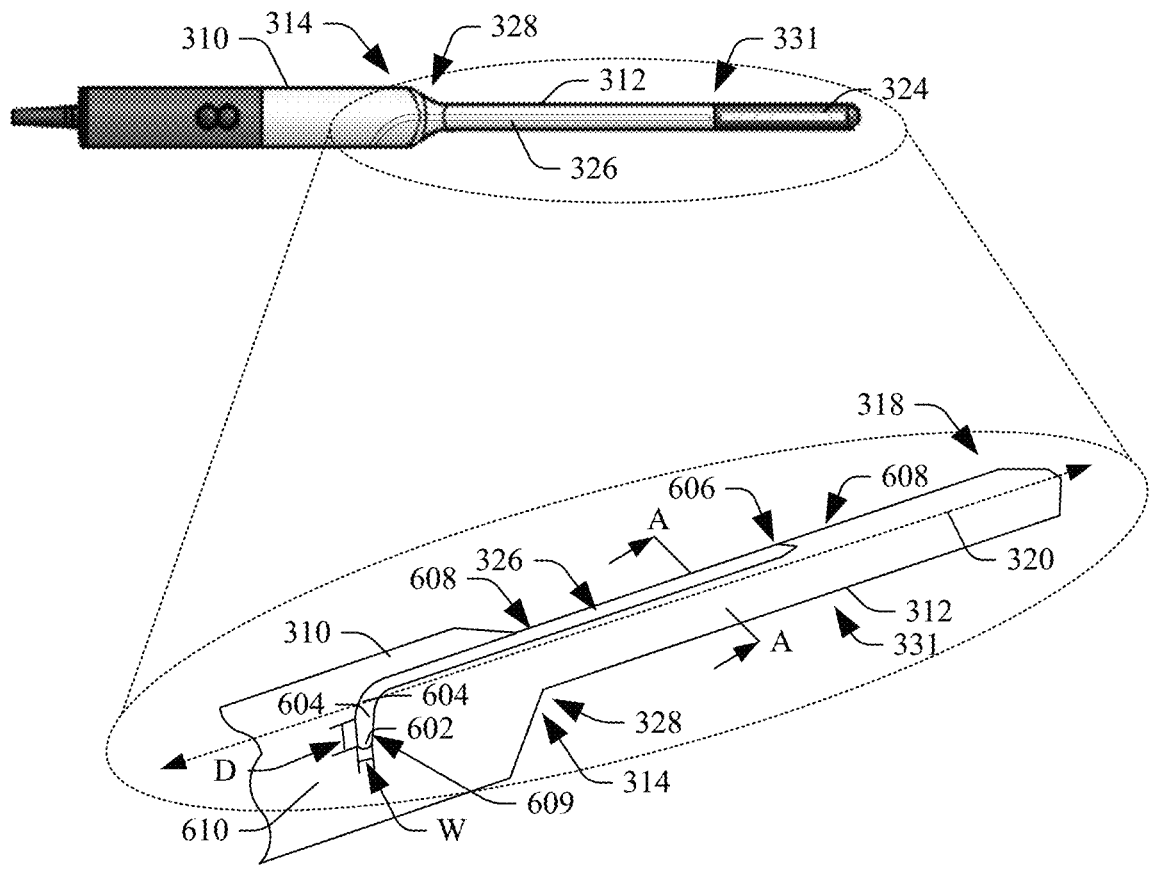
FIG. 6 illustrate a top down view of the probe of FIG. 4, showing the recess.

FIGS. 4, 5 and 6 show an example of the probe 304. FIG. 4 shows a perspective view of the probe 304. FIG. 5 shows a side view of the probe 304. FIG. 6 shows a top down view of the probe 304, including a magnified sub-portion of the probe 304, showing an example of the channel 326 of the probe 304 in a perspective view.

In FIG. 6, the channel 326 extends along the long axis 320 from the 314/328 interface toward the end region 318. The channel includes a floor 602 and side walls 604. In this example, the floor 602 is concave shaped and the side walls 604 are planar. In other embodiments, the floor 602 and/or the side walls 604 are otherwise shaped. Briefly turning to FIGS. 12A, 12B and 12C, a cross sectional view along line A-A showing a concave floor 602 and planar side walls 604 is illustrated.

Returning to FIG. 6, a depth "D" and a width "W" of the channel 326 is the same (within a predetermined tolerance) from the 314/328 interface up to a region 606. In a variation, D and/or W can vary along this extent. At the region 606, the depth decreases as the floor 602 in the channel 326 rises or inclines up to a surface 608 of the out perimeter housing 331 where there is no longer a recess in the outer perimeter housing 331. The rise in the floor 602 can be linear and/or non-linear, continuous and/or stepped, abrupt and/or gradual, etc. In a variation, this portion of the floor 602 does not rise.

In the illustrated example, the channel 326 also extends from the 314/328 interface through the handle 310 to an opening 609 at a side 610 of the handle 310. In a variation, the channel 326 ends at the 314/328 interface or elsewhere. In the illustrated example, this portion of the channel 326 first extends linearly through the handle 310 and then curves to the side 610 of the handle 310. D and W are the same through the shaft 312 and the handle 310. In a variation, the geometry of the channel 326 in the handle 310 can be different, e.g., non-linear portion, an irregular portion, different D and/or W, etc.

Figure 7:
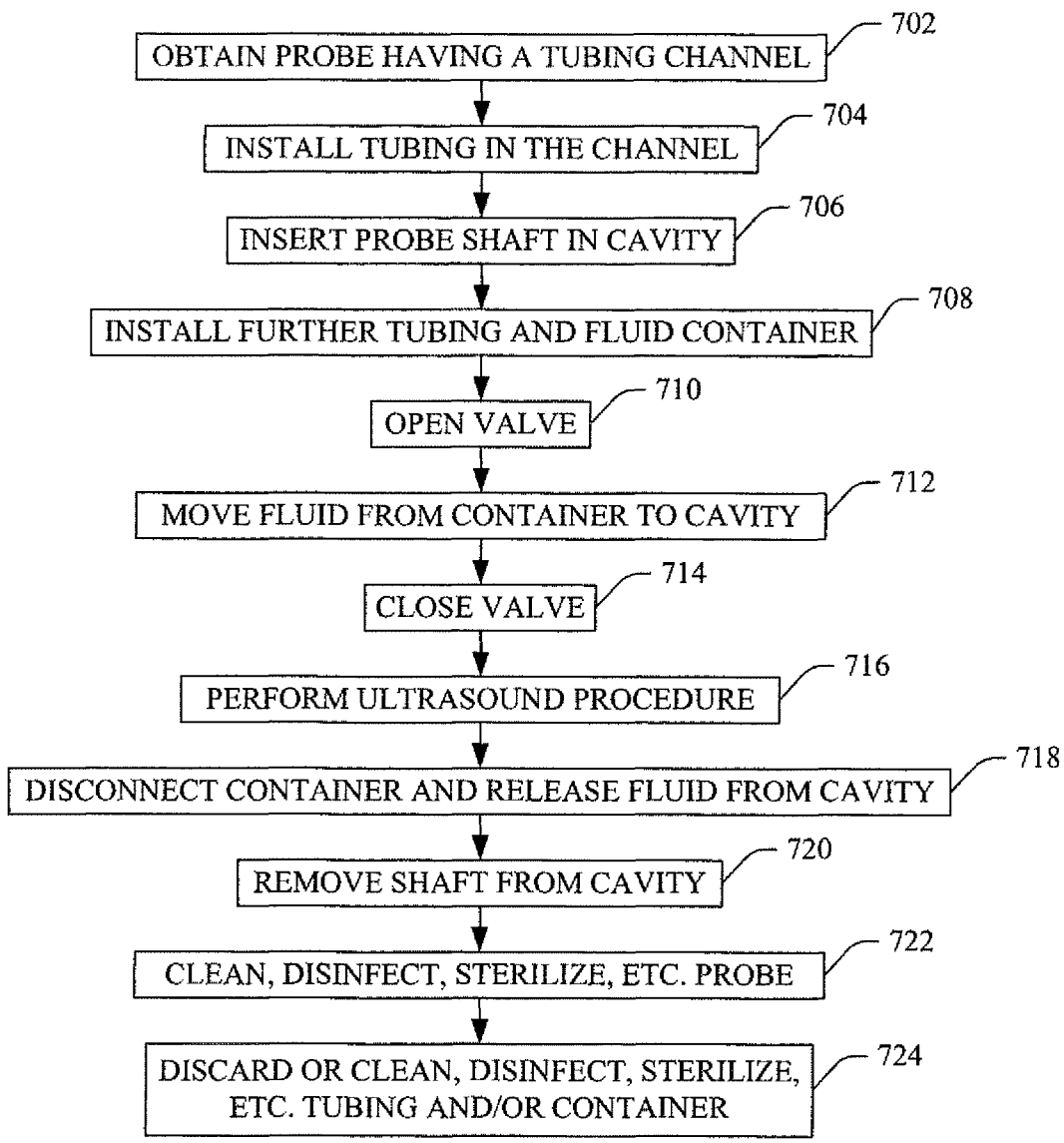
FIG. 7 describes an example method in accordance with an embodiment described herein.

FIG. 7 illustrates a method for employing the probe 304 in connection with a colorectal procedural. FIGS. 8, 9, 10 and 11 are referenced for graphical illustration.

It is to be appreciated that the order of the following acts is provided for explanatory purposes and is not limiting. As such, one or more of the following acts may occur in a different order. Furthermore, one or more of the following acts may be omitted and/or one or more additional acts may be added.

Figure 8:
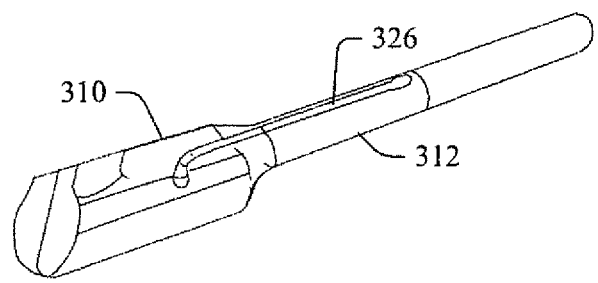
FIG. 8 schematically illustrates a sub-portion of the probe showing the recess without tubing installed therein.

At 702, a cleaned, disinfected, sterilized, etc. probe 304 is obtained for the procedure within a cavity. FIG. 8 shows an example of a sub-portion of the probe 304, showing the handle 310, the shaft 312, and the channel 326.

Figure 9:
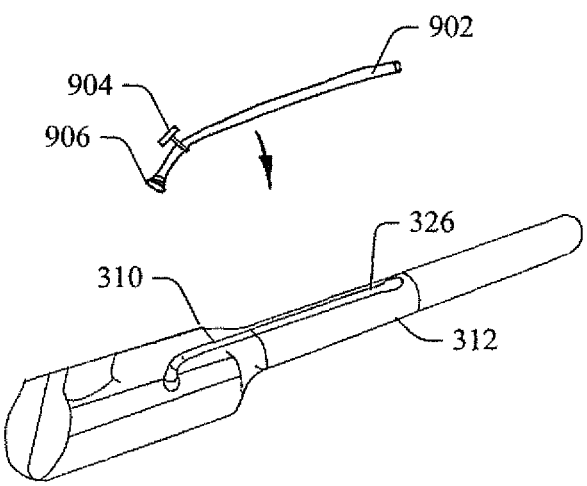
FIG. 9 schematically illustrates the sub-portion of the probe of FIG. 8 showing the tubing being installed in the recess.
Figure 10:
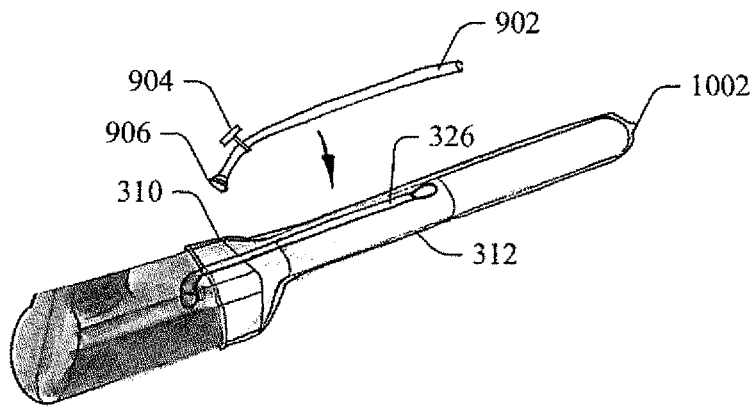
FIG. 10 schematically illustrates the sub-portion of the probe of FIG. 8 showing the tubing being installed in the recess over a sheath.

At 704, tubing is installed in the channel 326. FIG. 9 shows an example in which tubing 902, which includes a valve 904 and a connector 906, is installed directly into the channel 326. FIG. 10 shows an example in which a sheath 1002 is first installed over the shaft 312 and then the tubing 902 is installed in the channel 326 over the sheath 1002. In either instance, a sheath (balloon, water standoff, etc.) may also be installed over the shaft 312 and the installed tubing 902.

At 706, the probe shaft 312 is inserted into the rectum. FIG. 10 shows the shaft 312 inserted into a cavity 1102 inside of a human being (e.g., the rectum).

Figure 11:
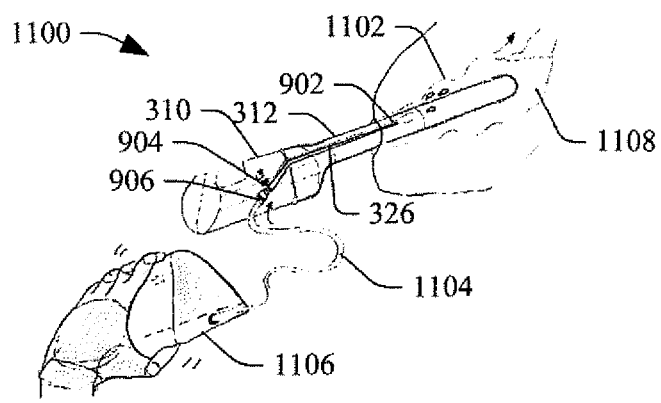
FIG. 11 shows further tubing removable connected to the tubing of FIG. 10.

At 708, further tubing is removably connected to the installed tubing, if not already connected thereto, where the further tubing is also connected to a depressible container holding a fluid. FIG. 11 shows further tubing 1104 removably connected to the port 906 and a depressible container 1106 holding a fluid 1108. Together, the probe 304, the tubings 902 and 1104, and the container 1106 are referred to herein as system 1100.

At 710, the valve 904 is opened. FIG. 10 shows the rotational movement of the valve 9004 to open the valve 904.

At 712, the depressible container 1106 is actuated which pushes the fluid 1108 through the tubings 1104 and 902 to the cavity 1102. FIG. 11 shows a user squeezing the depressible container 1106 to push the fluid 1108.

At 714, the valve 904 is closed.

At 716, an ultrasound procedure is performed.

At 718, the container 1106 (and/or further tubing 1104) is then disconnected from the port 906 and the valve 904 is opened, allowing the fluid 1108 in the cavity 1102 to egress out of the tubing 902.

At 720, the probe shaft 312 is removed from the cavity 1102.

At 722, the probe 304, including the channel 326, is cleaned, disinfected, sterilized, etc. for another the procedure.

At 724, the tubings 902 and 1104, sheath 1002, and/or the container 1105 are discarded or cleaned, disinfected, sterilized, etc.

FIG. 12A shows the cross section of the shaft 312 along line A-A of FIG. 6 without the tubing 902 installed in the channel 326 and with the cover 1002 over the channel 326. FIG. 12B shows the cross section with the tubing 902 partially installed in the channel 326. In this example, installing the tubing 902 in the channel 326 pushes the cover into the channel 326. FIG. 12C shows the cross section with the tubing 902 installed in the channel 326. In FIG. 12C, the tubing rests against the floor 602 and the side walls 604 with the cover 1002 therebetween. In this example, D is greater than a diameter of the tubing 902 and W is the same or slightly larger (e.g., 0-100 microns) than the diameter of the tubing 902.

FIGS. 13A, 13B and 13C show a variation in which the side walls 604 include an arc portion 1302. A distance 1304 between ends of the arc portion 1302 is less than the diameter of the tubing 902. As such, as shown in FIG. 13B, the tubing 902 is deformed (e.g., compressed) as the tubing 902 passes the ends of the arc portion 1302 when being installed in the channel 326, although it still pushes the cover 1002 into the channel 326. Installing the tubing 902 is this example requires the user to urge (e.g., push) the tubing 902 passed the ends of the arc portion 1302. Once inside the channel 326, as shown in FIG. 13C, the tubing shape returns and the ends of the arc portion 1302 inhibit the tubing 902 from coming out of the channel 326 on its own. To remove installed tubing 902, the user urges (e.g., but this time pulls) the tubing 902 passed the ends of the arc portion 1302.

FIGS. 14A, 14B and 14C show another variation. In this variation, the side walls 604 are planar as shown in FIGS. 6, 12A-C and 13A-C, and the floor 602 is also planar, and not arc shaped. This variation further includes features such as nubs 1402 along the side walls 604. The illustrated location, size, number, etc. of nubs 1402 is for illustrative purposes. That is in other variations other locations, above and below the illustrated location along the depth, large or smaller nubs 1402, only a single nub 1402 on one side or multiple on both sides, etc. are contemplated. A distance 1403 between the nubs 1402 is less than the diameter of the tubing 902. As such, as shown in FIG. 14B, the tubing 902 is deformed as the tubing 902 passes the nubs 1402 when being installed in the channel 326, e.g., when pushed into the channel 326. Once inside the channel 326, as shown in FIG. 13C, the nubs 1402 secure the tubing 902 in place with the cover 1002 between the tubing 902 and the nubs 1402. To remove installed tubing 902, the user again urges (e.g., but this time pulls) the tubing 902 passed the nubs 1402.

Combinations of the above and/or other variations are also contemplated herein. For example, a variation of FIGS. 14A-C could have the side walls 604 that are convex in place of or in addition to the nubs 1402, where the minimum distance between the side walls 604 is less than the diameter of the tubing 902. Other features besides nubs are also contemplated herein. For example, another feature is a tacky surface of the floor 602 and/or walls 604. Another feature is a set screw or the like. Another feature is an elastic band. Another feature is a mechanical door that opens and closes. Another feature is the tubing 902 itself, which expands when filed with the fluid 1108 to make the diameter of the tubing 902 large than the opening and/or width of the channel 326. Still other combinations, variations and/or other features are contemplated herein.

Figure 15:
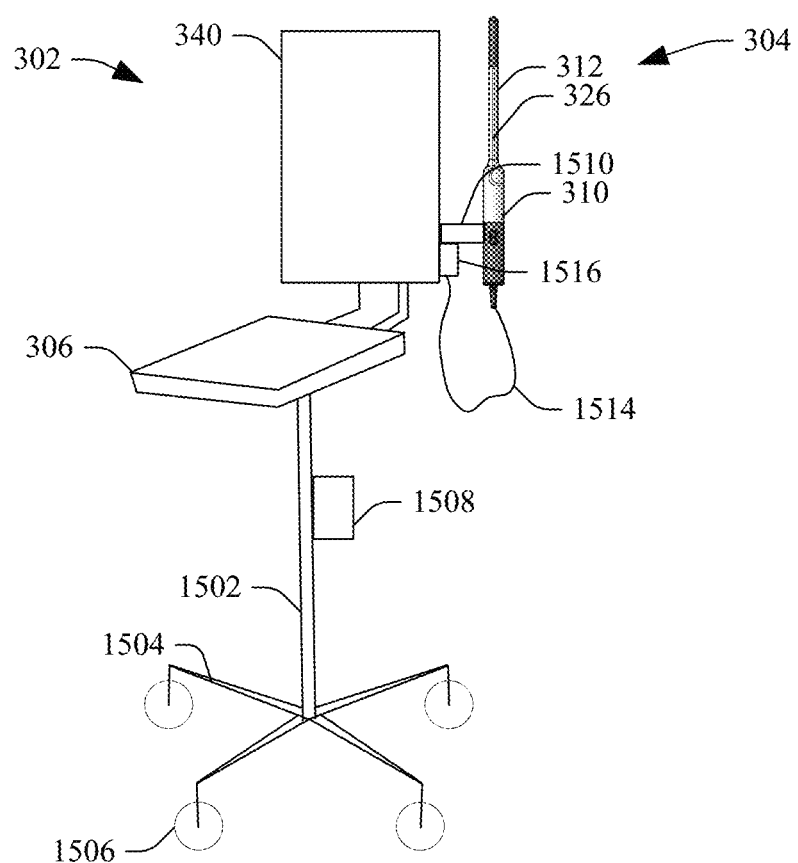
FIG. 15 illustrates an example of the ultrasound imaging system.

FIG. 15 illustrates an example of the ultrasound imaging system 302 with the probe 304 with the channel 326 in the shaft 312. In this example, the display 340 and the console 306 are separate devices attached to a mobile cart 1502, which includes a base 1504 with movers 1506 such as wheels, casters, etc. A portable energy source 1508 such as a rechargeable and/or non-rechargeable battery pack and/or other source supplies power for the system 302. A probe support 1510 is affixed to the cart 1502 and supports at least the probe 304. A cable 1514 extends from the handle 310 to a probe interface 1516 of the console 306. In another configuration, the ultrasound imaging system 302 rests on a table, desk, etc., and does not include movers and is not attached to a cart.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. A system, comprising:
    an ultrasound imaging probe, including:
        an elongate shaft including a first end region and a second end region, which is located opposite the first end region along a long axis of the probe;
        a handle including a side affixed to the first end region of the elongate shaft;
        a transducer array disposed at the second end region of the elongate shaft
        a recess, including:
            a first sub-section that is part of an outer perimeter of the elongate shaft and extends along the long axis of the probe along a top of the elongate shaft from the first end region to the second end region;
            a second sub-section that is part of an outer perimeter of the handle, extends along the long axis of the probe along a top of a first sub-portion of the handle, curves along the top towards a side of the handle for a second sub-portion of the handle, and terminates at the side of the handle.

2. The system of claim 1, wherein the recess comprises:
    a floor having a non-zero depth (D).

3. The system of claim 2, wherein the recess comprises:
    side walls extending from the floor to a non-recessed surface, defining a non-zero width (W) therebetween.

4. The system of claim 1, wherein the first sub-section in the shaft has a first width and a first depth, and the second sub-section in the handle has a second width and a second depth.

5. The system of claim 4, wherein the first and second widths are equal and the first and second depths are equal.

6. The system of claim 1, wherein the side of the handle includes an opening, and the second sub-section terminates at the opening.

7. The system of claim 2, wherein the floor inclines in the first sub-section to the non-recessed surface at an end of the second end region of the elongate shaft.

8. The system of claim 3, wherein the side walls are separated from each other by a distance that varies with the depth, and a first distance between the side walls at an interface of the side walls with the non-recessed surface is a smallest distance between the side walls along the depth.

9. The system of claim 8, further comprising:
    tubing with first and second open ends, wherein the tubing is removably installed in the channel.

10. The system of claim 9, wherein the tubing has a diameter, and the first distance is less than the diameter.

11. The system of claim 3, wherein the side walls are separated from each other by a constant distance.

12. The system of claim 11, further comprising:
    tubing with first and second open ends, wherein the tubing is removably installed in the channel.

13. The system of claim 12, wherein the side walls include a feature configured to secure the tubing in the channel.

14. The system of claim 9, further comprising:
    a fluid container holding an acoustic medium, wherein the fluid container is connected to one of the first or second open ends of the tubing such that the fluid in the fluid container flows into the first or second open end of the tubing and out of the other of the second or first open end of the tubing.

15. A method, comprising:
    receiving an acoustic fluid at one end of a tubing installed in a first recess of a top surface of a handle of an ultrasound imaging probe,
    wherein an opening of the tubing receiving the acoustic fluid is at a side of the handle,
    routing the acoustic fluid through the tubing, which extends in a second recess, on an outer surface of an elongate shaft that extends along a long axis of the ultrasound imaging probe: and
    expelling the acoustic fluid out of an opposing end of the tubing at an end of the elongate shaft before a transducer array.

16. The method of claim 15, wherein the tubing lies over a cover disposed over the elongate ultrasound imaging probe and the recess.

17. The method of claim 15, wherein the acoustic fluid is expelled into and expands a sheath that is over the elongate ultrasound imaging probe.

18. The method of claim 15, wherein the acoustic fluid directly contacts walls of the cavity.

19. An ultrasound imaging probe, comprising:
a tubular section with a long axis and a first recess extending along an entirety of the long axis;
a first end portion affixed to a first end of the tubular section;
a second end portion affixed to a second opposing end of the tubular section;
one or more transducer elements disposed at one of the first or second end portions; and
a handle disposed at the other end of the first or second end portions,
wherein the recess extends along an entirety of a top of the tubular section and has a floor that inclines up to a non-recessed region of the one of the first or second end portions only at an end region of the first recess next to the one or more transducer elements.

20. The ultrasound imaging probe of claim 19, wherein the handle includes a second recess that extends entirely along a top of a sub-portion of the handle from a side wall of the handle to the first recess.

21. The ultrasound imaging probe of claim 19, further comprising: at least one feature in the first recess configured to keep an instrument installed in the first recess.

22. The ultrasound imaging probe of claim 21, wherein the instrument is tubing.

23. The ultrasound imaging probe of claim 19, wherein the probe is a colorectal probe.

* * * * *